United States Patent [19]

Fukazawa

[11] Patent Number: 5,527,707
[45] Date of Patent: Jun. 18, 1996

[54] METHOD OF ANALYZING IMPURITIES IN THE SURFACE OF A SEMICONDUCTOR WAFER

[75] Inventor: Yuji Fukazawa, Yokohama, Japan

[73] Assignee: Kabushiki Kaisha Toshiba, Kawasaki, Japan

[21] Appl. No.: 359,555

[22] Filed: Dec. 20, 1994

[30] Foreign Application Priority Data

Dec. 21, 1993  [JP]  Japan ................................ 5-320705

[51] Int. Cl.$^6$ .................................................. G01N 23/223
[52] U.S. Cl. ........................ 436/72; 436/73; 436/172; 436/180; 250/492.2; 378/45
[58] Field of Search ...................... 436/72, 73, 172, 436/178, 180, 175; 250/473.1, 487.1, 492.1; 378/45–47, 49, 83

[56] References Cited

U.S. PATENT DOCUMENTS

| 4,584,886 | 4/1986 | Matsunaga et al. | 73/863 |
| 5,006,382 | 4/1991 | Squire | 428/35.7 |
| 5,148,457 | 9/1992 | Kubota et al. | 378/70 |
| 5,305,366 | 4/1994 | Nakahara et al. | 378/45 |
| 5,476,006 | 12/1995 | Jujii et al. | 73/105 |

OTHER PUBLICATIONS

Watanabe et al. AN 1994:123797 HCAPLUS.
Ariga et al. AN 1991:220389 HCAPLUS.
Taguchi, S. et al. AN 1995:339100 HCAPLUS.
Rapsomanikis, et al, AN 1988: 460533 HCAPLUS.
Pietsch et al.; AN 1994:228076 HCAPLUS.

*Primary Examiner*—Jeffrey R. Snay
*Attorney, Agent, or Firm*—Finnegan, Henderson, Farabow, Garrett & Dunner

[57] ABSTRACT

A silicon wafer is placed in an atmosphere of hydro-fluoric acid vapor, dissolving an oxide film formed on a surface of the wafer and forming solution drops containing impurities. A Teflon plate is put on the surface of the silicon wafer, such that its hydrophilic surface is set in contact with the HF solution drops. The drops are transferred to the hydrophilic surface of the Teflon plate. Fluorescent X rays are applied to the hydrophilic surface of the Teflon plate and totally reflected the hydrophilic surface. The energy peaks of the impurities, including aluminum whose energy peak is similar to that of silicon, are detected from the fluorescent X rays totally reflected. Also, the distribution of the impurities in the surface of the wafer are determined from the fluorescent X rays.

4 Claims, 3 Drawing Sheets

METHOD OF ANALYZING IMPURITIES IN THE SURFACE OF A SEMICONDUCTOR WAFER

BACKGROUND OF THE INVENTION

1. Field of the Invention

The present invention relates to a method of analyzing impurities existing in the surface of a semiconductor substrate, by using X rays, and more particularly to a method of analyzing aluminum existing in the surface of a silicon substrate, by using totally reflected fluorescent X rays.

2. Description of the Related Art

Hitherto, metal impurities in the surface of a silicon wafer have been analyzed by a so-called VPO-AA method, in which the metal impurities are dissolved with a hydrofluoric acid (HF) solution, and the metal impurities dissolved in the HF solution are analyzed by means of atomic absorption spectrometry. In this method, the HF solution is applied on the surface of the wafer, thereby collecting the impurities are collected from the surface of the wafer. With this method it is impossible to determine the plane distribution of the metal impurities.

A so-called TRXRF method is known, which is a non-destructive method of analyzing metal impurities in the surface of a silicon wafer. In the TRXRF method, fluorescent X rays are applied to the silicon wafer surface and the metal impurities are analyzed based on the X-rays reflected from the silicon wafer surface. With this method it is possible to determine plane impurity distribution in a spot size of about 10 mm.

FIG. 1 is a graph representing a distribution of metal impurities in the surface of a silicon wafer, which has been detected by means of the TRXRF method. Each metal impurity is identified by the energy which is indicated on the abscissa. The quantity of each metal impurity is determined from the strength of the reflected X rays which is plotted on the ordinate. The TRXRF method has a problem, however. Metals having almost the same energy can hardly be distinguished from one another. For example, silicon (Si) and aluminum (Al) have almost the same energy. The energy peak (1.49 keV) of Al overlaps that (1.74 keV) of silicon. Consequently, aluminum in the silicon wafer surface can hardly be detected. In brief, the TRXRF method can determine the distribution of metal impurities in a silicon wafer surface, but fails to identify the impurities with sufficient accuracy.

SUMMARY OF THE INVENTION

The object of the present invention is to provide a method of analyzing impurities in the surface of a semiconductor substrate, which can not only determine the distribution of metal impurities in a silicon wafer surface, but also identify the impurities with high accuracy.

According to the invention, there is provided a method of analyzing impurities in a surface of a semiconductor substrate, comprising the steps of: dissolving impurities existing in the surface of the semiconductor substrate, to form drops of containing the impurities on the surface of the semiconductor substrate; transferring the drops from the surface of the semiconductor substrate to a surface of sample substrate made of a material different from the semiconductor substrate and more hydrophilic than the surface of the semiconductor substrate; applying fluorescent X rays to the surface of the sample substrate; and analyzing the impurities based on the fluorescent x rays reflected from the surface of the sample substrate.

Since the impurities are easily transferred from the semiconductor substrate onto the sample substrate of a different material, it is possible to identify the impurity having almost the same energy as the material of the semiconductor substrate.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

DETAILED DESCRIPTION OF THE PREFERRED EMBODIMENTS

An embodiment of this invention will be described, with reference to the accompanying drawings.

Figure 1:
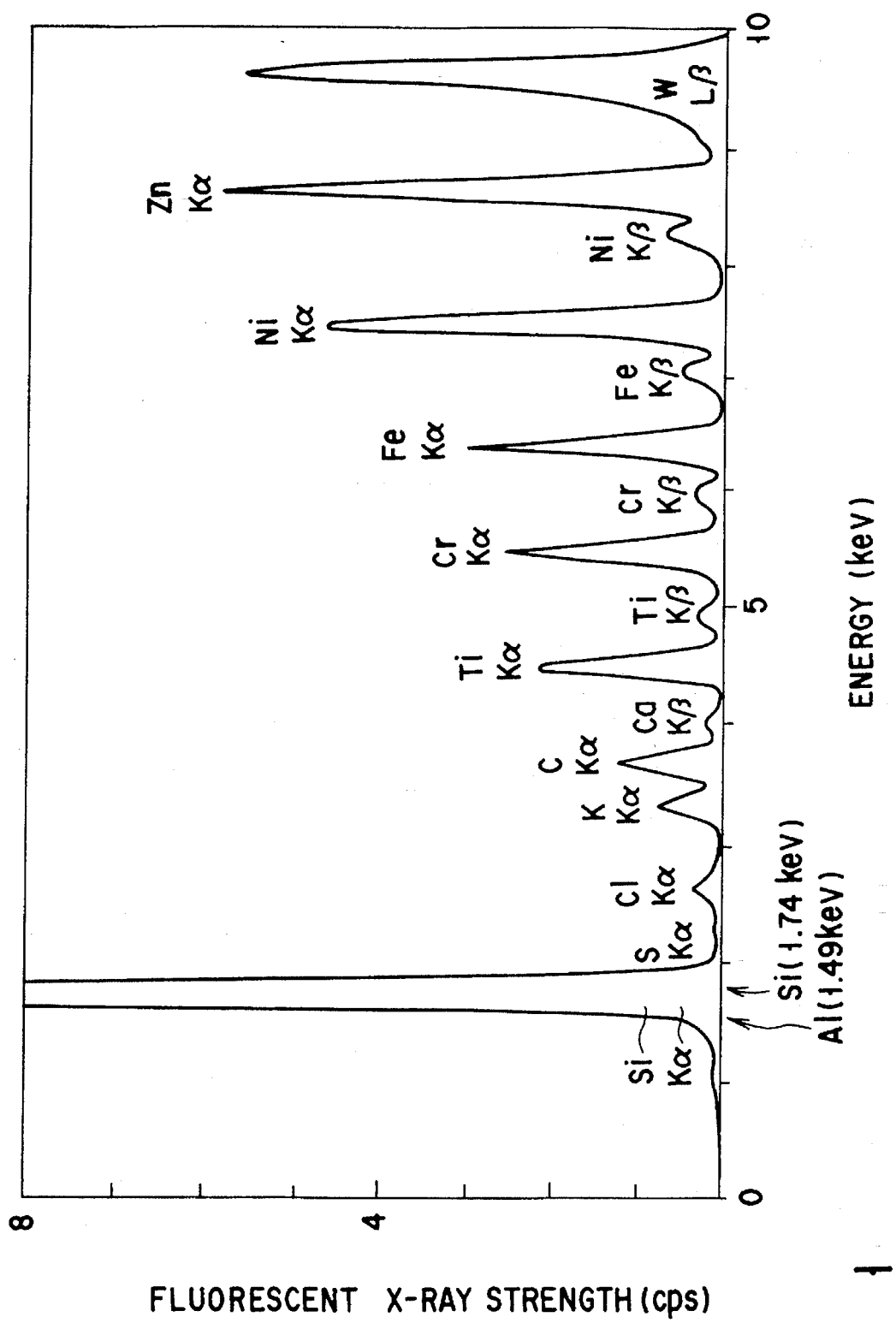
FIG. 1 is a graph representing a distribution of metal impurities in the surface of a silicon wafer, said distribution having detected by means of the TRXRF method.
Figure 2A:
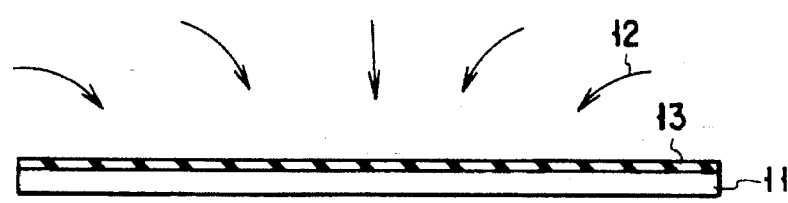
FIGS. 2A to 2E are diagrams for explaining a method of analyzing impurities, which is an embodiment of the present invention.
Figure 2B:
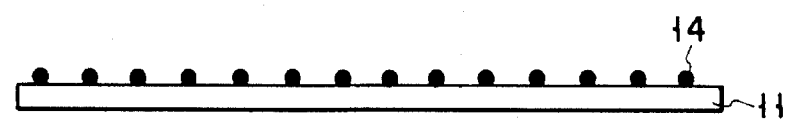

First, as shown in FIG. 2A, a silicon (Si) wafer 11 is left to stand for about one hour in an about 49% HF (Hydrofluoric Acid) atmosphere 12 to dissolve the oxide film 13 on the surface of the wafer 11 with the HF vapor 12, thus forming drops 14 of HF solution, as shown in FIG. 2B. The drops of HF solution contain the metal impurities desorbed from the surface of the wafer 11, such as iron (Fe), aluminum (Al), calcium (Ca) and the like. The HF solution drops 14 are almost spherical since the surface of the silicon wafer 11 hydrophobic. Their size can be controlled by changing the time in which the HF vapor 12 is supplied into the process chamber.

Figure 2C:
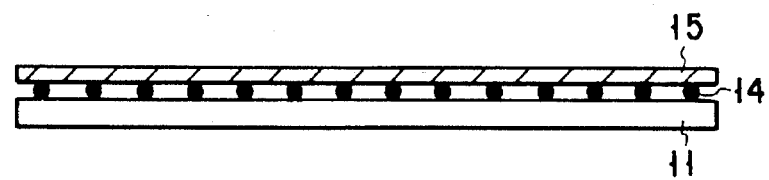
Figure 2D:
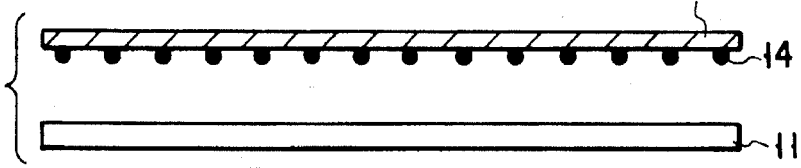

Thereafter, a Teflon plate 15 having a surface made hydrophilic is placed on the surface of the silicon wafer 11, such that hydrophilic surface is set in contact with the HF solution drops 14 as is illustrated in FIG. 2C. As shown in FIG. 2D, the Teflon plate 15 is then removed from the silicon wafer 11, with the drops 14 adhered to its hydrophilic surface. In other words, the HF solution drops 14 are transferred from the surface of the silicon wafer 11 to the surface of the Teflon plate 15. The drops 14 are readily transferred since the surface of the silicon wafer 11 is hydrophobic and applies repulsive force on the drops 14, whereas the surface of the Teflon plate 15 has been rendered hydrophilic and attracts the drops 14.

Figure 2E:
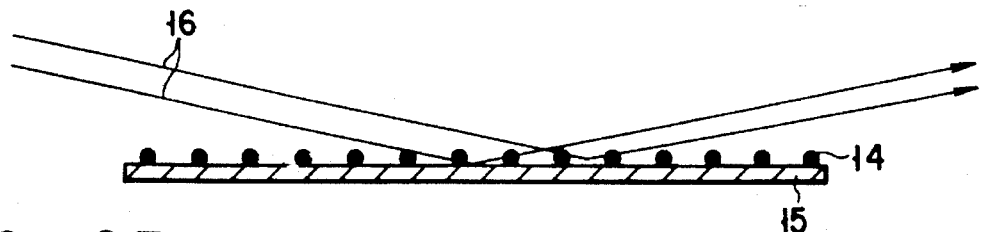
Figure 3:
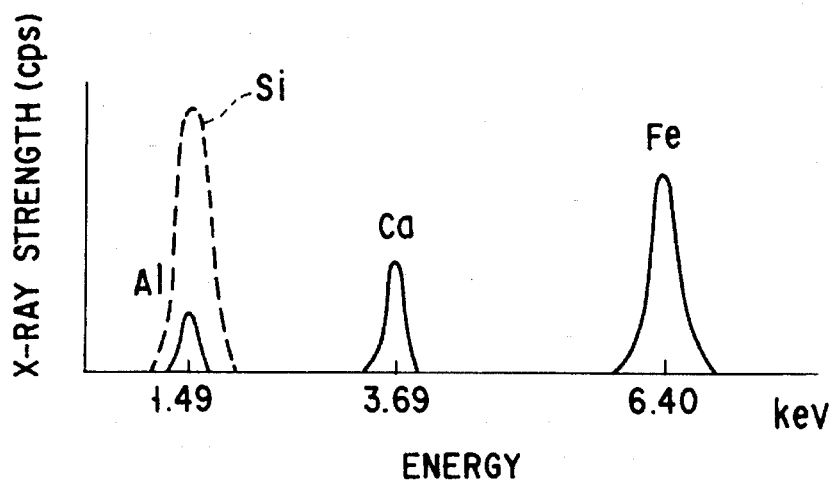
FIG. 3 is a graph showing the results of the analysis performed by using the method according to the invention.
Figure 4:
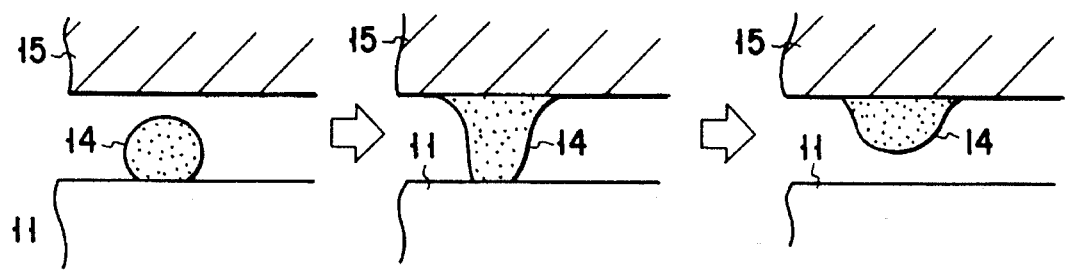
FIG. 4 is a diagram for explaining how to transfer solution drops from the surface of a wafer to the surface of a Teflon plate in the method according to the invention.

As shown in FIG. 2E, total reflection fluorescent X rays 16 are applied to the hydrophilic surface of the Teflon plate 15. The fluorescent X rays 16 are totally reflected from the hydrophilic surface of the Teflon plate 15 and pass through the HF solution drops 14. From these X rays 16 totally reflected, the metal impurities contained in the drops 14 are detected and analyzed.

Now that the HF solution drops 14 are on the Teflon plate 15, not on the silicon wafer 11, the fluorescent X-rays 16 reflected from the plate 15 contain no components representing the energy peak of Si. Unlike in the TRXRF method, the energy peak of Al can therefore be detected distinctly despite that it is almost the same as that of Si. In this way, the metal impurities existing in the surface of the silicon wafer 11 can be analyzed with high accuracy.

It should be noted that the Teflon plate 15 is heated a little before it is placed on the surface of the silicon wafer 11. The HF solution drops 14 are therefore adsorbed to the Teflon plate 15 is a more accurate pattern than otherwise. Thus, the impurity distribution detected from the fluorescent X rays totally reflected from the hydrophilic surface of the Teflon plate 15 is faithful to the impurity distribution in the surface of the wafer 11. Hence, the metal impurities in the surface of the silicon wafer 11 can be analyzed accurately, based on the impurity distribution detected from the fluorescent X rays.

In the present invention, the Teflon plate 15 may be replaced by a plate made of any other material that is more hydrophilic than the material of a semiconductor substrate.

If the distribution of the metal impurities need not be detected, and the total amount of the metal impurities only needs to be determined, there is no need to heat the Teflon plate 15. In this case, the drops 14 of HF solution may move on the surface of the Teflon plate 15, impairing the accuracy of transferring the distribution of the impurities from the silicon wafer 11 to the Teflon plate 15. This does not matter, however, in respect of the measuring of the impurity total amount. All drops 14 are transferred from the wafer 11 to the plate 15 even if the temperature of the plate 15 is relatively low.

A metal impurity such as copper (Cu) cannot be well dissolved with HF vapor 12. In order to analyze copper existing in the surface of the silicon wafer 11 substrate, ozone gas ($O_3$) may be supplied into the process chamber (not shown), together with the HF vapor 12, thereby to dissolve copper.

As described above, the impurities in the surface of a silicon wafer is dissolved with HF vapor, forming HF solution drops containing the impurities on the surface of the wafer. These drops are transferred from the wafer to a Teflon plate, whose surface is more hydrophilic than the wafer surface. Fluorescent X rays are applied to the hydrophilic surface of the Teflon plate and are totally reflected from the Teflon plate surface on which the solution drops exist. From these X rays, the metal impurities contained in the drops are detected and analyzed. In this way, any metal impurity in the surface of the silicon wafer can be analyzed with high accuracy. Even the energy peak of Al can be detected distinctly despite that it is almost the same as that of Si.

Since the Teflon plate is heated a little before it is placed on the surface of the silicon wafer, the HF solution drops are adsorbed to the Teflon plate in an accurate pattern. The impurity distribution detected from the reflected fluorescent X rays is faithful to the impurity distribution in the surface of the silicon wafer. The metal impurities in the surface of the wafer can therefore be analyzed accurately, based on the impurity distribution.

The present invention is not limited to the embodiment described above. Rather, various changes and modification can be made within the scope and spirit of the invention.

As has been described, the present invention can provide a method of analyzing impurities in the surface of a semiconductor substrate, which can not only determine the distribution of metal impurities in a silicon wafer surface, but also identify the impurities with high accuracy.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A method of analyzing distribution of impurities existing in a surface of a semiconductor substrate, comprising the steps of:

dissolving impurities existing in the surface of the semiconductor substrate, to form a plurality of drops containing the impurities in a pattern on the surface of the semiconductor substrate, the pattern corresponding to the distribution of impurities in the semiconductor substrate;

transferring the drops from the surface of the semiconductor substrate to a sample substrate surface, the sample substrate being made of material different from the semiconductor substrate and more hydrophilic than the semiconductor substrate, so that the drops are transferred in the pattern to the sample substrate surface;

irradiating the drops on the sample substrate surface with X-rays to induce X-ray fluorescence; and analyzing the impurities contained in each of the drops based on the X-ray fluorescence induced by the X-ray radiation and determining distribution of the impurities on the semiconductor substrate based on the analysis.

2. The method according to claim 1, wherein said impurities are dissolved by exposing the surface of the semiconductor substrate to an atmosphere of hydrofluoric acid vapor.

3. The method according to claim 1, wherein said impurities are dissolved by exposing the surface of the semiconductor substrate to an atmosphere of hydrofluoric acid vapor, while applying ozone gas onto the surface of the semiconductor substrate.

4. The method according to claim 1, wherein the drops are transferred from the surface of the semiconductor substrate to the surface of sample substrate, while the sample substrate is being heated.

* * * * *